United States Patent [19]

Vaguine

[11] 4,397,314

[45] Aug. 9, 1983

[54] METHOD AND APPARATUS FOR CONTROLLING AND OPTIMIZING THE HEATING PATTERN FOR A HYPERTHERMIA SYSTEM

[75] Inventor: Victor A. Vaguine, Dallas, Tex.

[73] Assignee: Clini-Therm Corporation, Dallas, Tex.

[21] Appl. No.: 289,127

[22] Filed: Aug. 3, 1981

[51] Int. Cl.³ ............................................. A61N 1/40
[52] U.S. Cl. .................................... 128/399; 128/401; 128/736; 128/783; 128/804
[58] Field of Search ........... 128/399, 400, 401, 419 N, 128/422, 736, 783, 804

[56] References Cited
U.S. PATENT DOCUMENTS 4,210,152  7/1980  Berry .................................... 128/804
4,311,154  1/1982  Sterzer et al. ........................ 128/736

Primary Examiner—Richard J. Apley
Assistant Examiner—George Yanulis
Attorney, Agent, or Firm—Richards, Harris & Medlock

[57] ABSTRACT

A hyperthermia treatment system has multiple applicators and multiple temperature sensors for controlling the operation of the hyperthermia system. A temperature sensor probe implanted within a tumor provides a temperature signal for controlling and optimizing the power input to multiple applicators to maintain the system output during the treatment period at a predetermined control temperature. Temperature sensors implanted in the region of the healthy tissue provide temperature signals to override the controls providing power input to the applicators to prevent injury to healthy tissues. Individual microwave applicators are evaluated during the hyperthermia treatment to determine their effect on the overall heating pattern for optimizing the heating pattern.

10 Claims, 8 Drawing Figures

METHOD AND APPARATUS FOR CONTROLLING AND OPTIMIZING THE HEATING PATTERN FOR A HYPERTHERMIA SYSTEM

TECHNICAL FIELD

This invention relates to a method and apparatus for controlling and optimizing the heating pattern for a hyperthermia system, and more particularly to multiple temperature sensors implanted in both normal tissue and tumors for controlling and optimizing the heating pattern produced by multiple microwave or ultrasound applicators.

BACKGROUND ART

Hyperthermia is the heating of living tissue for therapeutic purposes. Hyperthermia has been used as a method of treating cancer by means of raising the temperature of a tumor locally, the region of the body in which the tumor is located, or the whole body. It has long been known that high heat can contribute to the natural regression and/or remission of tumors. Because of its effect on cancer cells, hyperthermia may be used as an independent therapy or in conjunction with other cancer therapies, such as radiation, surgery, chemotherapy, and immunotherapy to enhance the effectiveness of these therapeutic modalities.

Current hyperthermia techniques used in cancer therapy include regional perfusion with heated fluids, microwave heating, fluid immersion, low frequency (RF) current fields, and ultrasound. Three of the most common types of currently used hyperthermia techniques involve radio frequency, microwaves and ultrasound. Radio frequency and microwave equipment may be used for local, regional and whole body heating. Ultrasound can be used for local and regional heating. Perfusion, the passing of a heated fluid through a limb, is limited to treatment of a limb. Immersion techniques involve immersing the body in a hot wax or hot water solution.

Hyperthermia systems have been developed utilizing direct contact microwave applicators. The depth of penetration of the microwave energy is frequency-dependent, and penetration is also a function of tissue composition and anatomical structure. The design of the microwave applicator influences the thermal distribution. In addition, sharp changes in patient contour within the treatment area (as in the head and neck) will have a strong influence on the thermal distribution.

In hyperthermia treatment systems such as radiofrequency, microwave and ultrasound, healthy normal tissue is heated as well as the tumor cells. Since normal healthy cells can be destroyed by elevated temperatures as well as cancer cells of a tumor, it is important during the hyperthermia treatment to maintain the temperature of the healthy tissues below the point in which damage is likely to occur while maintaining the tumor at elevated temperatures necessary for treatment. In such hyperthermia treatment techniques the temperature in the tumor will exceed the temperature of the surrounding healthy tissue, since the healthy tissue is cooled somewhat by the flow of blood through the entire body. Typically, tumors are not cooled by the flow of blood. Hyperthermia treatment involves the raising of the tumor temperature to a temperature on the order of 45° C. for a prescribed period of time in a course of which treatment cancer cells (which normally cannot effectively withstand these temperatures) are damaged. During treatment, an effort is made to keep normal tissues at lower temperatures. Typically, tumors have a poor blood flow system as present in normal healthy tissue which carries off the heat of hyperthermia treatment. Healthy tissue is characterized by a developed blood vessel network and normal physiological response to heat, a phenomenon known as vasodilation where the blood may increase threefold after five minutes of heating. By way of contrast, tumors typically are characterized by a damaged blood vessel network and a collapsing blood flow during heating.

Hyperthermia treatment systems have been developed which operate only with a single microwave applicator and multiple temperature sensors. In such systems, only one sensor is used to actively control the hyperthermia system; this sensor is implanted in the tumor and provides temperature information to a computer for feedback and control of microwave power level and applicator. The other implanted temperature sensors perform a passive monitoring function, assisting the hyperthermia system operator in decision making during the treatment.

Hyperthermia systems have also been developed which employ up to twelve applicators, but independent power controls are not available for each applicator to optimize the heating pattern. These systems generally utilize only a single non-invasive temperature sensor.

Another type of hyperthermia system has been developed, as an annular phase array system, and it has up to eight individual microwave applicators and eight temperature sensor probes. As in other existing systems, the system has no independent power control for each applicator and only one of the temperature sensors planted within the tumor performs any active control function.

A need has thus arisen for a method and apparatus for optimizing the heating pattern in a microwave or ultrasound hyperthermia system for controlling the power input to single and multiple applicators in response to temperature control information from sensors detecting the temperature within a tumor and the surrounding normal tissue.

SUMMARY OF THE INVENTION

The apparatus and method of the present invention for optimizing the heating pattern for a hyperthermia system is an improvement over the above described prior art apparatus and method. Multiple applicators, utilizing ultrasound or microwave energy, are placed in direct contact with the surface of the human tissue treatment area. The applicators are typically operated in the direct contact mode by placement directly upon an elastic cooling belt containing a circulating cooling liquid to carry the heat of hyperthermia treatment away from the surface of the healthy tissue. Temperature sensors are implanted in the normal tissue in the vicinity of the tumor, and temperature sensors are also planted directly within the tumor. The temperature sensors are built from extremely low loss materials, providing the required transparency to microwave fields and "non-perturbing" properties. One suitable temperature sensor is based upon a semiconductor/fiberoptic technique claimed in U.S. Pat. No. 4,136,566, issued on Jan. 30, 1979 to D. A. Christensen. The temperature sensor probes may be inserted into the normal tissue and area of the tumor through a plastic catheter with a closed end.

One of the multiple temperature sensors is assigned a control function for the hyperthermia system. The temperature sensor or sensors implanted in a tumor provide direct feedback to a microwave or ultrasonic generator providing power input into the multiple applicators for controlling the tumor temperature. Additional temperature sensors are assigned a protective function. These temperature sensors are implanted in the normal healthy tissue and as the temperature of the normal tissue approaches a threshold value, one of these protective probes assumes the control function that protects the normal tissues from overheating by controlling the power input to the microwave or ultrasonic applicators to effect the heating pattern.

In another aspect of the present invention, an optimum heating pattern for a treatment may be realized by real time measurements of the effect of temperature produced by each of the applicators in each measured location. In the typical treatment, the hyperthermia treatment time is from thirty to one hundred and twenty minutes; therefore, there is sufficient time to diagnose the heating pattern by turning "off" and "on" each one of the multiple applicators in the system for a short period of time. In the incoherent mode of operation, the overall heating pattern is additive, or a combination of the individual heating patterns produced by each individual applicator. Therefore, the specific contribution of an applicator to the overall heating pattern can be easily evaluated by the simple manipulation of its input power, i.e., turning the power to the applicator "off" and "on". As a result one can determine the derivitives of the temperature with respect to time for each applicator, and for each probe (location) it is possible to establish the contribution of each applicator to the heating pattern. Since the blood perfusion condition changes during the hyperthermia treatment, it requires a repetition of the diagnostic cycle for determining the contribution of each applicator to the overall heating pattern.

In another aspect of the present invention, a more detailed three dimensional temperature distribution is possible by having multiple temperature sensors implanted in one catheter in a linear array. The tip of each of the individual sensor probes may be fixed in a predetermined relationship within a protective plastic sleeve. The individual temperature sensors are connected through an optic fiber to control apparatus.

In addition to controlling the power input to each of the multiple applicators, the temperature sensors may be utilized for controlling the liquid circulating through a cooling belt. Temperatures sensors implanted near the surface of the skin may be utilized to monitor the temperature in the area of the surface of the skin.

DESCRIPTION OF DRAWINGS

For a more complete understanding of the present invention and the advantages and features thereof, reference is now made to the accompanying Detailed Description taken in conjunction with the following FIGURES in which.

DETAILED DESCRIPTION

Figure 1:
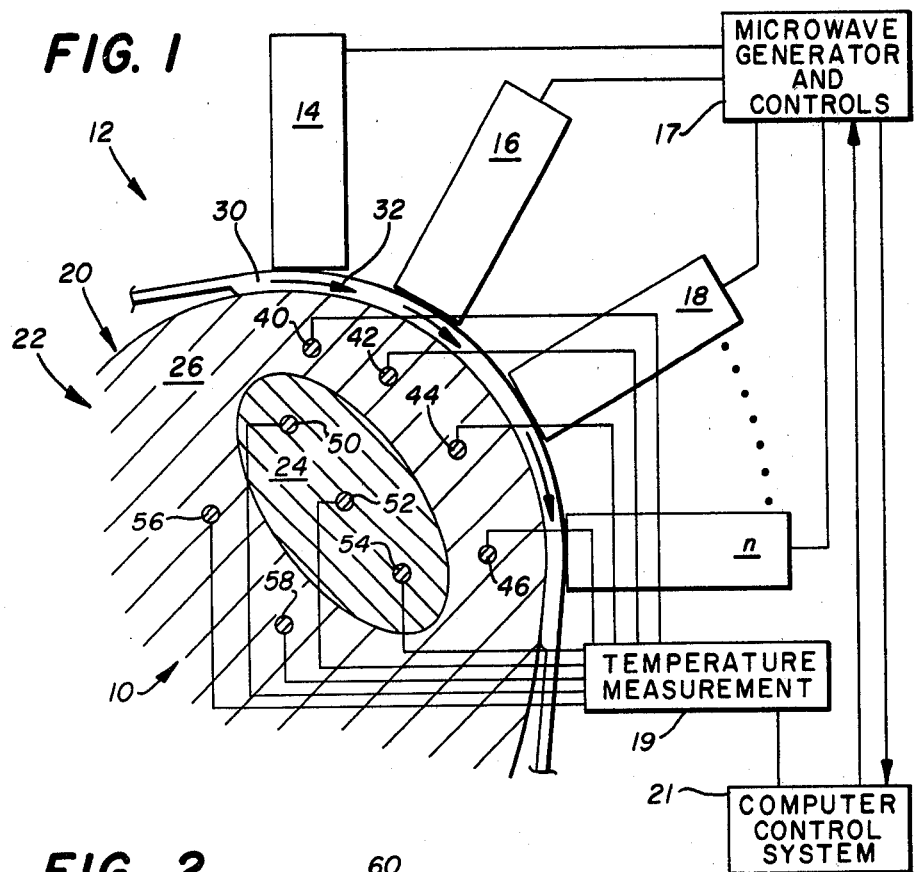
FIG. 1 is a cross-sectional view of multiple applicators and implanted multiple temperature sensors in a hyperthermia treatment system.

FIG. 1 illustrates a hyperthermia treatment system utilizing multiple temperature sensors, generally identified by the reference numeral 10, for controlling the power input to multiple applicators, generally identified by the reference numeral 12. Individual treatment applicators 14, 16 and 18-N may be arranged in a suitable geometric configuration to conform to the surface 20 of the treatment area 22. The individual hyperthermia applicators 14, 16 and 18-N are representative of individual applicators which apply microwave energy for the treatment, though ultrasound applicators could also be used. The treatment area 22 is the site of a malignant tumor 24 surrounded by healthy tissue 26. The applicators 14, 16 and 18-N are brought into direct contact with the surface 20 of the treatment area 22 through a liquid cooling belt 28, containing a liquid 30, such as distilled water, circulating in the direction indicated by the arrow 32. The circulating cooling liquid 30 is cooled as it exits the belt 28 to carry off the heat from the surface area 20 to help maintain the temperature of the normal tissue below a certain threshold value. The cooling effect of the liquid cooling belt 28 can be controlled by temperature information signals from multiple skin temperature sensors (not illustrated) beneath or in the vicinity of belt 28 to a control unit (not illustrated) for the cooling belt 28. Such cooling control units are well known to those knowledgeable about hyperthermia treatment systems.

Temperature sensors 10 can be assigned one of four possible functions: (1) tumor temperature control; (2) normal tissue temperature control; (3) passive temperature monitoring and (4) skin cooling control. The multiple temperature sensors 10 includes individual sensors 40, 42, 44 and 46 implanted in the region of normal tissue between the source of microwave or ultrasound energy, applicators 14, 16 and 18-N, and the malignant tumor 24. The temperature sensors 40-46 function to monitor and/or control temperature in normal tissue 26 by controlling the power input to the applicators 14, 16 and 18-N to prevent the normal tissue from being raised to a temperature beyond the threshold temperature to avoid permanent damage. Temperature sensors 50, 52 and 54 are illustrated implanted in the malignant tumor 24, and sensor 52 functions to control the tumor temperature and sensors 50 and 54 function to passively monitor the temperature at the edges of the tumor 24. The temperature sensor 52 serves a control function involving the raising of the tumor temperature to approximately 45° C. to effect the cancer cells. Additional temperature sensors 56 and 58 may be planted in the region of normal tissue 26 in the site of tumor 24 distal from the source of microwave or ultrasound energy. The temperature sensors 56 and 58 function to passively monitor temperature in these locations.

The applicators 14, 16 and 18-N are connected to a microwave generator 17 for providing microwave power input and control of the power input to each applicator. The temperature sensors 40–58 are sensed and measured by a temperature measurement device 19 which provides temperature information signals to a computer control system 21. The computer control system 21 maintains the predetermined therapeutic control temperature, typically 45° C., in the tumor and provides control to redistribute or optimize the power input levels to keep the temperature in the normal tissue below a predetermined threshold level, typically 42° C. or less. In lieu of or in addition to the computer control system 21, the hyperthermia system may have means for a clinical operator to intervene to control the power input level to the microwave or ultrasound applicators.

Any one of several computer systems may be utilized as the computer control system 21. One such system is a Motorola M68000 computer system. One standard configuration of the system 21 includes the following: a sixteen (16) bit Motorola M68000 computer, thirty-two (32)K bytes of data memory, thirty-two (32)K bytes of program memory, a CRT display and keyboard, and an alpha-numeric and graphic printer/plotter. The predetermined tumor control temperature, e.g., 45° C., and normal tissue threshold temperature, e.g. 42° C., are entered through the keyboard into the data memory unit of the computer control system 21. The operator may also input data identifying a temperature sensor with an applicator having the greatest influence in the area of a sensor, e.g., sensor 40 and applicator 14. The CRT display provides means for displaying the real time temperature profile in the treatment area as sensed by multiple sensors 10. The printer/plotter provides a record of the treatment sensor.

The temperature measurement device 19 is a microprocessor controlled thermal dosimetry unit and provides simultaneously temperature measurement of each of the sensors 10. The temperature control signals are transmitted from temperature measurement circuit 19 to the M68000 computer of computer control system 21 for processing in accordance with the program stored in the program memory unit and the sensor identification data input by the operator. The computer is programmed to monitor the output from sensors 10 to control the power from the microwave or ultrasound generator to each of the multiple applicators. The operator may also intervene to make control adjustments. The power input to each applicator is adjusted to reach and maintain the tumor temperature at its predetermined therapeutic control value, while allowing the predetermined threshold value for normal tissue to override the tumor temperature control signals. If the threshold temperature is reached, the power input is decreased for all or selected ones of the multiple applicators. By way of example, if sensor 56 reaches the threshold value of 42° C., the computer control system 21 is programmed to redistribute the power from applicator 14 to the other applicators 12.

Figure 2:
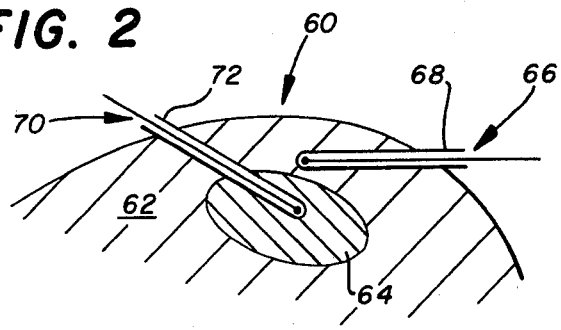
FIG. 2 is a cross-sectional view of a treatment area of human tissue with multiple temperature sensors.

FIG. 2 illustrates a treatment area of human tissue 60, including normal tissue 62 and malignant tumor tissue 64. A fiber optic temperature sensor 66 is implanted into the region of normal tissue 62 through a protective closed end plastic catheter 68. A second fiber optic temperature sensor 70 is inserted into the center of the malignant tumor 64 through a protective closed end plastic catheter 72. The temperature sensors 66 and 70 actively monitor the temperature in the normal tissue and malignant tumor, respectively, which can retrieve information as used to control the power input to the multiple applicators 12 through the microwave generator 17, illustrated in FIG. 1 and described hereinabove.

Figure 3:
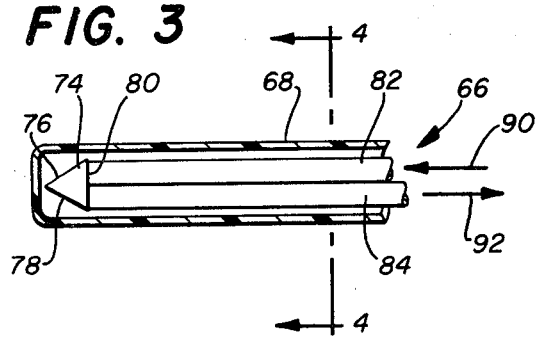
FIG. 3 is a cross-sectional view of a human tissue area for treatment with a linear array temperature sensor probe.
Figure 4:
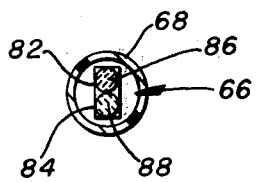
FIG. 4 is a partially cutaway side view of a temperature sensor of the present invention.

FIGS. 3 and 4 illustrate the type of fiber optic temperature sensor 66 described above. The temperature sensors 66 and 70 are typical of the nonperturbing fiber optic temperature sensor probes utilized in the present invention for sensing temperature in the presence of an electromagnetic field. U.S. Pat. No. 4,136,566 describes such a semiconductor temperature probe which may be utilized as the temperature sensor probe of the present invention. The temperature probe includes a semiconductor crystal 74, selected and fabricated as a reflecting-/refracting device as part of the optical component of the system so as to reflect/refract radiant energy through the semiconductor from a monochromatic transmitter (not illustrated) to an intensity detector (not illustrated). A suitable semiconductor sensor 74 may be fabricated from a gallium arsenide (GaAs) material. A semiconductor sensor 74 is fabricated as a prism having reflective faces 76 and 78 and an incident face 80. A semiconductor sensor 74 is optically coupled to the ends of optical fibers 82 and 84, more particularly to the cores 86, 88 therein, respectively. Other temperature measuring means may be utilized to implement the present invention than the semiconductor temperature probe described above. The temperature measurement means in a microwave hyperthermia system should be nonperturbing to the electromagnetic field.

In operation, monochromatic radiant energy is transmitted through optic fiber 82 in the direction indicated by the arrow 90 and is reflected a first time at the face 76 and a second time at the face 78 as a transmitted ray 92 through fiber optic cable 84. The radiant energy absorbed by the semiconductor sensor 74 is a function of the temperature. The intensity of the transmitted ray 92 will be diminished as the temperature of the semiconductor 74 is increased. The intensity of the transmitted ray 92 is readable as a temperature by a receiver display unit (not illustrated).

Figure 5:
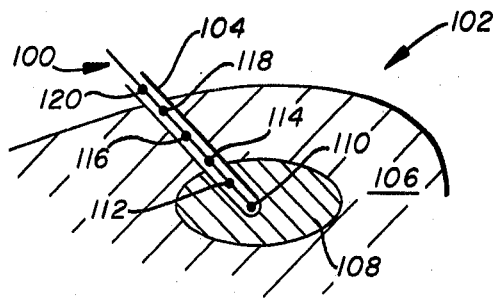
FIG. 5 is a cross-sectional view of the temperature sensor of FIG. 4.

FIG. 5 illustrates an improved fiber optic temperature sensor probe 100 for use in obtaining a more detailed three dimensional temperature distribution in a treatment area 102. The temperature sensor probe 100 is inserted through a closed plastic catheter 104 through a normal tissue region 106 into a malignant tumor 108. A linear array of multiple temperature sensors 112, 114, 116, 118 and 120 extend from the center of the tumor 108 through the region of healthy tissue 106 to the area immediately outside the surface of the treatment area 102. The temperature sensors 110 and 112 provide an indication of the temperature at the center and near the surface of the tumor 108. The temperature sensors 114, 116 and 118 provide a linear indication of the temperature from near the site of the tumor 108 to near the surface of the treatment area 102. The temperature sensor 120 may be provided outside the surface of the skin of the treatment area 102.

Figure 6:
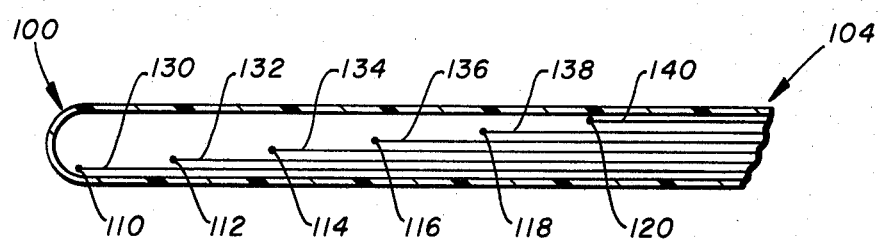
FIG. 6 is an enlarged side view of a multiple temperature sensor probe of the present invention.
Figure 7:
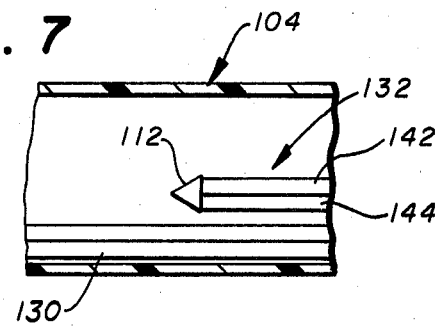
FIG. 7 is an enlarged sectional view of region A illustrated in FIG. 6.
Figure 8:
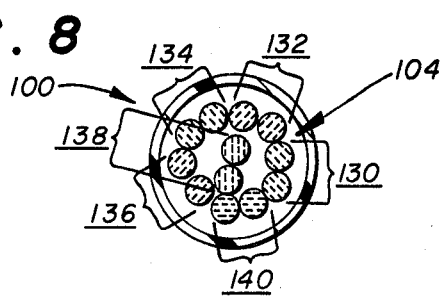
FIG. 8 is a cross-sectional view of the temperature sensor probe illustrated in FIG. 7.

The improved linear array temperature probe 100 is further illustrated in FIGS. 6–8. As illustrated in FIG. 6, the temperature sensor probe 100 is ensheathed in a protection plastic catheter 104. Each of the sensors 110–120 is connected by pairs of fiber optic cables 130, 132, 134, 136, 138 and 140 respectively. An enlarged view of the temperature sensor 112 and its pair of fiber optical cables 132 is illustrated in FIG. 7. The diameter of the plastic catheter 104 is sufficient to accommodate the multiple fiber optic cables 130, 132, 134, 136, 138 and 140. As illustrated in FIG. 8, the protective plastic shield 104 may readily accommodate the bundle of fiber optic cables 130-140. The fiber optic cable 132 includes a first cable 142 for transmitting the monochromatic radiant energy to the temperature sensor 112, which may be fabricated from gallium arsenide. A second fiber optic cable 144 transmits the reflected ray, the intensity of which is a function of the temperature of the semiconductor sensor 112.

In a typical hyperthermia treatment, the patient is subjected to electromagnetic radiation for a period of thirty (30) to one hundred and twenty (120) minutes. In a microwave hyperthermia treatment system operating in the incoherent mode, there is sufficient time to diagnose the heating pattern by turning each applicator sequentially "on" and "off" for a short period of time. The following basic equation can be used in an alternate embodiment of the present invention for development of a software algorithm for solution by the computer control system 21 to optimize the overall heating pattern:

$$\rho c \frac{dT}{dt} = \nabla^2 + W_b C_b (T_a - T_b) + q_0 + \sum_{i=1}^{n} q_i, \text{ where}$$

T-temperature measured by one of the temperature sensors;
$Q_O$-methabolic generation rate
$Q_i$ heat generation rate by applicator number;
$T_a$-arterial temperature and proximity of the temperature sensor;
$T_b$-venial temperature in proximity of the temperature sensor;
$W_b$-blood profusion rate
$C_b$-specific heat of blood.

Assuming that the blood perfusion does not change during the "diagnostic" cycle, one can determine the contribution of each applicator to the derivitive dT/dt. As blood perfusions change during hyperthermia treatment, it requires a repetition of the diagnostic cycle to again determine the contribution of each applicator to the derivitive of the temperature.

As as example of a typical hyperthermia treatment session for the arrangement shown in FIG. 1, the prescribed treatment may call for thirty (30) minutes of radiation with the tumor raised to a control temperature of 45° C. and the threshold temperature for normal tissue set at 42° C. These two control values are keyboard entered into the data memory unit of the computer control system 21. The temperature information signal for the tumor is derived from sensor 52 and is feed to the temperature measurement circuit 19. The temperature measurement circuit 19 transmits the tumor temperature signal to the control system 21 to allow it to regulate the power input level to the applicators 14, 16 and 18-N. In one embodiment of the invention, the particular applicators having the greatest effect on the temperature of the tumor 24 may be determined by turning the individual applicators "off" and "on", or lowering and raising the power input level and observing the effect on the temperature of the tumor 24.

The temperature measurement device 19 also transmits the temperature signal from healthy tissue from sensors 40-46 to the control system 21 to protect healthy tissue from overheating. The threshold temperature level set in the control system 21 as keyboard entered data has priority over the control setting entered for the tumor treatment temperature. Thus, if the temperature equals the threshold setting of 42° C., the control system overrides the tumor control setting and redistributes the power input level to be applicators 14, 16 and 18-N to keep the temperature below the threshold level. For example, if the temperature sensor 40 indicates 42° C., the computer can decrease power to the microwave applicator 14 and increase power to the other applicators 16 and 18-N.

The hyperthermia treatment may require modifications in response to the temperature control information. Considering the clinical treatment prescribed above, in some clinical situations it may not be possible to elevate the tumor temperature to the desired level of 45° C. and also maintain the temperature of healthy tissue below 42° C. The multiple temperature sensors 40-58 enable the clinican to modify the treatment. Instead of a radiation treatment for thirty (30) minutes holding tumor temperature at 45° C. and the normal tissue at 42° C. or below, the treatment may last for sixty (60) minutes with the tumor at a temperature of 44° C. and the normal tissue held at a temperature of 42° C. or less. The printer/plotter unit of the computer system 21 makes a record of the treatment temperature during treatment by pulling temperature versus the time.

Although the preferred embodiments of the invention have been illustrated in the accompanying drawings and described in the foregoing Detailed Description, it will be understood that the invention is not to be limited to the embodiments disclosed, but is capable of numerous rearrangements, modifications and substitutions of parts and elements without departing from the spirit of the invention.

I claim:

1. In a microwave hyperthermia treatment system including a microwave power generator, a plurality of microwave applicators powered by the microwave power generator, and a power input control for each of the applicators to vary the power input to the applicators from the microwave power generator, wherein the improvement comprises:
    multiple temperature sensors for actively monitoring the temperatures in both the tumor and the region of normal tissue subject to treatment, including means for generating a temperature control signal for each of said sensors;
    a first means for generating a control signal to selected ones of the power input controls of the microwave applicators in response to said temperature control signal from said sensors for the tumor for maintaining the temperature within the tumor at a predetermined control temperature;
    a second means for generating a control signal to selected ones of the power input controls to the microwave applicators in response to a temperature control signal from said sensors in a region of normal tissue indicating a temperature in excess of a threshold temperature; and
    means for said second control signal to override said first control signal to decrease the power input to selected ones of said applicators, whereby the normal tissue is protected by keeping it below a predetermined threshold temperature while maintaining the temperature within the tumor at the temperature closest to the predetermined control temperature permitted by the power input to the microwave applicators.

2. The hyperthermia treatment system of claim 1, wherein said multiple temperature sensors for monitoring the temperature within the region of normal tissue and the region of the tumor comprises:

a plurality of semiconductor temperature sensors spaced a predetermined distance apart to form a linear array, each of said temperature sensors being connected by a pair of fiber optic cables to determine the temperature at each of the points where the semiconductor temperature sensors are located.

3. In a microwave hyperthermia treatment system including a microwave power generator, a plurality of microwave applicators powered by the microwave power generator, and a power input control for each of the applicators to vary the power input to the applicators from the microwave power generator, wherein the improvement comprises:

multiple temperature sensors for actively monitoring the temperatures in both the tumor and the region of normal tissue subject to treatment, including means for generating a temperature control signal for each of said sensors;

a first means for generating a control signal to the power input control to at least one of the microwave applicators in response to said temperature control signal from at least one of said sensors for the tumor for maintaining the temperature within the tumor at the predetermined control temperature;

a second means for generating a control signal to the power input control to at least one of the microwave applicators in response to a temperature control signal from at least one of said sensors in a region of normal tissue indicating a temperature in excess of a threshold temperature; and means for said second control signal to override said first control signal to decrease the power input to an applicator, whereby the normal tissue is protected by keeping it below a predetermined threshold temperature, the multiple microwave applicators being geometrically configured to be proximal the surface of a human tissue closest to the tumor.

4. The hyperthermia treatment system of claim 1 and further comprising:

means for cooling the surface of the treatment area; and means for controlling said cooling means in response to temperature information signals from said multiple temperature sensor probes.

5. The hyperthermia treatment system of claim 1 and further comprising:

means for cooling the skin area of the patient treatment area, including means for controlling said cooling means;

at least one temperature sensor for monitoring the temperature of the surface skin area; and means for regulating said cooling control means responsive to said skin temperature sensor.

6. A hyperthermia treatment system including an ultrasonic generator, a plurality of ultrasonic applicators, and a power input control to each of the applicators, wherein the improvement comprises:

multiple temperature sensors for actively monitoring the temperatures in both the tumor and normal tissue in a patient treatment area including means for generating a temperature control signal for each of said sensors;

a first means for generating a control signal to selected ones of the power input controls of the ultrasonic applicators in response to said temperature control signals from said sensors for the tumor for maintaining the temperature within the tumor at a controlled treatment temperature;

a second means for generating a control signal to selected ones of the power input controls to the ultrasonic applicators in response to a temperature control signal from the sensors in a region of normal tissue indicating a temperature in excess of a predetermined threshold temperature; and means for said second control signal to override said first control signal to decrease the power input to selected ones of said applicators, whereby the normal tissue is protected from overheating while maintaining the temperature within the tumor at the predetermined control treatment temperature.

7. A microwave hyperthermia treatment system, comprising:

a microwave power generator;

a plurality of microwave applicators connected to said microwave generator and distributed in a desired orientation;

means for individually controlling the power input from said microwave generator to each of said microwave applicators;

an electronic digital signal processing system, said system including an electronic digital signal processor, a data memory unit, a program memory unit, means for entering data to said data memory unit and a display means;

a plurality of nonperturbing temperature sensors, at least one of said sensors detecting the temperature in a tumor within a patient and at least another of said sensors detecting the temperature in normal tissue of a patient;

means for obtaining a tumor temperature control signal from said tumor sensor;

means for obtaining a normal temperature control signal from said normal sensor;

means for storing a predetermined therapeutic tumor control temperature in said data memory unit;

means for storing a predetermined normal tissue threshold temperature in said data memory unit; and means for applying said tumor temperature control signal and said normal tissue control signal to said electronic digital signal processor, said processor adjusting said power input control means to individually control the power input to each of said applicators in response to said tumor control signal for maintaining the tumor temperature at said predetermined tumor control temperature and said processor adjusting said power input control means in response to said normal tissue control signal exceeding said predetermined threshold value, whereby when said normal tissue control signal indicates a normal tissue temperature in excess of the threshold value, the power input to selected ones of said microwave applicators is decreased, overriding the tumor temperature control signal while optimizing the distribution of power input to the microwave applicators to maintain temperature in the tumor at the predetermined therapeutic tumor control temperature.

8. The microwave hyperthermia treatment system of claim 1 and further comprising:

means for operator control of said power input control means, such that the operator observing said display means may make real time adjustments to said power input control means for said microwave hyperthermia applicator.

9. In a hyperthermia treatment system including a power generator, a plurality of energy applicators powered by the power generator for transmitting energy to tissue, and a power input control for each of the applicators to vary the power input to the applicators from the power generator, wherein the improvement comprises:

at least one multiple semiconductor temperature sensor for use with a monochromatic light transmitter and a light intensity detector for providing multiple temperature measurements linearly along the sensor, said semiconductor temperature sensor including a plurality of semiconductor crystals spaced a predetermined distance apart along the central axis of a housing member and a pair of fiber optic cables connected to each of said semiconductor crystals for transmitting a monochromatic light to each of said crystals along one of said cables and transmitting the reflected light along the other of said cables to the light intensity detector, whereby a linear array of temperature is sensed along the axis of the sensor, the temperatures in both the tumor and the region of normal tissue subject to treatment being actively monitored, including means for generating a temperature control signal for each temperature sensed by one of said sensors;

a first means for generating a control signal to selected ones of the power input controls of the applicators in response to said temperature control signal from said sensors for the tumor for maintaining a temperature within the tumor at a predetermined control temperature;

a second means for generating a control signal to selected ones of the power input controls to the applicators in response to a temperature control signal from said sensors in a region of normal tissue indicating a temperature in excess of a threshold temperature;

means for said second control signal to override said first control signal to decrease the power input to selected ones of said applicators, whereby the normal tissue is protected by keeping it below the predetermined threshold temperature while maintaining the temperature within the tumor at the predetermined control temperature.

10. In a hyperthermia treatment system including a power generator, a plurality of applicators powered by the power generator, and a power input control for each of the applicators to vary the energy input to the applicators from the power generator, wherein the improvement comprises:

multiple temperature sensors for actively monitoring the temperatures of both the tumor and the region of normal tissue subject to treatment, including means for generating a temperature control signal for each of said sensors;

a first means for generating a control signal to selected ones of the power input controls of the applicators in response to said temperature control signal from said sensors for the tumor for maintaining the temperature within the tumor at a predetermined control temperature;

a second means for generating a control signal to selected ones of the power input controls of the applicators in response to a temperature control signal from said sensors in a region of normal tissue indicating a temperature in excess of a threshold temperature; and means for determining the heating effects of each of the individual applicator in the tumor and normal tissue, said means for determining the heating effects compensating for variation in the heating effects due to blood perfusion; and means for optimizing the energy input to each of the applicators by use of the power input controls to protect the normal tissue by keeping it below the predetermined threshold temperature while maintaining the temperature within the tumor at the predetermined control temperature.

* * * * *

UNITED STATES PATENT AND TRADEMARK OFFICE
CERTIFICATE OF CORRECTION

PATENT NO. : 4,397,314
DATED : August 9, 1983
INVENTOR(S) : Victor A. Vaguine

It is certified that error appears in the above—identified patent and that said Letters Patent is hereby corrected as shown below:

Column 5, line 36, change "simultaneously" to --simultaneous--.

Column 6, line 61, change "protection" to --protective--.

Column 8, line 2, change "be" to --the--.

Column 12, line 31, change "applicator" to --applicators--.

Signed and Sealed this

Twentieth Day of December 1983

[SEAL]

Attest:

GERALD J. MOSSINGHOFF

Attesting Officer   Commissioner of Patents and Trademarks